(12) United States Patent
Gurtner et al.

(10) Patent No.: US 9,150,045 B2
(45) Date of Patent: Oct. 6, 2015

(54) METHOD AND DEVICE FOR SURGICAL MARKING

(75) Inventors: Geoffrey C. Gurtner, Stanford, CA (US); Joseph Rimsa, Palo Alto, CA (US)

(73) Assignee: NOVADAQ TECHNOLOGIES INC., Mississauga (CA)

( * ) Notice: Subject to any disclaimer, the term of this patent is extended or adjusted under 35 U.S.C. 154(b) by 708 days.

(21) Appl. No.: 13/363,097

(22) Filed: Jan. 31, 2012

(65) Prior Publication Data
US 2013/0197358 A1    Aug. 1, 2013

(51) Int. Cl.
*B43K 8/00* (2006.01)
*A61B 19/00* (2006.01)
*B43K 8/10* (2006.01)
*B43K 8/03* (2006.01)
*B43K 8/06* (2006.01)
*B43K 23/12* (2006.01)
*B43K 29/08* (2006.01)

(52) U.S. Cl.
CPC . *B43K 8/003* (2013.01); *B43K 8/03* (2013.01); *B43K 8/06* (2013.01); *B43K 8/10* (2013.01); *B43K 23/12* (2013.01); *B43K 29/08* (2013.01); *A61B 2019/5404* (2013.01); *A61B 2019/545* (2013.01); *A61B 2019/5441* (2013.01)

(58) Field of Classification Search
USPC .................. 401/132, 134, 196, 40–42; 604/3; 606/116
See application file for complete search history.

(56) References Cited

U.S. PATENT DOCUMENTS

| 5,433,545 A * | 7/1995 | Keil ................................. 401/40 |
| 5,746,815 A | 5/1998 | Caputo |
| 6,027,271 A * | 2/2000 | Barosso et al. .................. 401/40 |
| 6,056,737 A | 5/2000 | Rosen |
| 6,972,022 B1 | 12/2005 | Griffin |
| 2004/0240925 A1 | 12/2004 | Iida et al. |
| 2006/0249690 A1 | 11/2006 | Pfister |
| 2008/0247807 A1 | 10/2008 | Whitehorn |
| 2010/0168561 A1 | 7/2010 | Anderson |

FOREIGN PATENT DOCUMENTS

| EP | 1 266 770 A1 | 12/2002 |
| GB | 2343187 | 5/2000 |
| WO | 9602192 | 2/1996 |
| WO | 2010/054219 A2 | 5/2010 |

OTHER PUBLICATIONS

International Search Report for counterpart application No. PCT/US2013/024011 completed on Mar. 18, 2013 and mailed on Apr. 15, 2013.

* cited by examiner

*Primary Examiner* — David Walczak
(74) *Attorney, Agent, or Firm* — Oliff PLC

(57) ABSTRACT

A surgical marking pen may include a pen body, a first chamber within the pen body containing at least one powdered dye, a second chamber within the pen body and separated from the first chamber, and a tip in fluid communication with the first chamber or the second chamber. The second container contains a solvent, and the first chamber and the second chamber are selectively placeable into fluid communication with one another. The at least one powdered dye and the solvent, when mixed, form a dye solution which is disposable upon a skin or tissue surface and is able to be visualized simultaneously by a user in ambient light and with a fluorescence imager.

27 Claims, 1 Drawing Sheet

METHOD AND DEVICE FOR SURGICAL MARKING

FIELD OF THE INVENTION

The present invention relates generally to medical devices used for marking tissue. More particularly, the present invention relates to surgical markers that mark skin with an ink that can be observed visually without any aids and by a fluorescent sensitive imaging system.

BACKGROUND OF THE INVENTION

There are several surgical procedures, such as cardiac bypass, fat grafting, and flap reconstruction to name a few, whose success relies heavily upon the revascularization or reprofusion of the surgical site.

One technique for evaluating the vascularization or reprofusion of the surgical site or area of interest is to use near infrared fluoroscopy equipment such as the SPY® Imaging System (Novadaq Technologies, Inc., FL) which is used to visualize blood flow in vessels and micro-vessels in real-time during a surgical procedure.

The SPY® Imaging System exposes an area of interest with near infrared light and records and displays the fluorescence stimulated by the light. For vascularization studies, the fluorescence comes from an intravenous injection of the fluorescent dye, i.e., Indocyanine Green (ICG), that bonds with the proteins in blood. Once in the circulatory system, the infrared light from the SPY® system penetrates deep into the area of interest causing the dye in the area to fluoresce. The camera viewing the area detects the invisible fluorescence and the system processes the information and displays it for the surgeon. The brighter the displayed area, the more blood flow while the darker the area, the lower the blood flow, if any.

One short coming of the system is the integration of the image on the display to that of the surgical site. Because the camera is tuned to be most sensitive to the invisible fluorescence wavelength, normally visible features such as skin anatomy or markings from surgical pens are not viewable on the display of the system simultaneously with the fluorescent image. As a result, it is difficult for the surgeon to relate the exact area of interest to the image on the SPY® display. More importantly however, any images or data recorded/stored from the SPY® system can't be related to features or planning marks made by surgical pens.

Without the requirement for the mark from a pen to be simultaneously visible to both a user and a fluorescence camera, the need for such a device for a surgical application may be unnecessary. Use of the SPY® Imaging System to evaluate and document the revascularization of a surgical site has created such a need.

SUMMARY OF THE INVENTION

Generally, a surgical marking pen which may enable visualization simultaneously by a user without aid of any additional or specialized equipment (e.g., with the naked eye) and with a fluorescent imager or camera may comprise a pen body having a first chamber within the pen body containing at least one powdered dye and a second chamber separated from the first chamber within the pen body and containing a solvent, where the first chamber and second chamber are selectively placed into fluid communication with one another, and a fibrous tip in fluid communication with the first or second chamber, wherein the at least one powdered dye and solvent, when mixed, forms a dye solution which is disposable upon a skin or tissue surface.

The specialized surgical marking pen having the mixed dye solution may be applied along one or more marks to a skin or tissue surface and then visualized simultaneously without aid and with a fluorescence imager. Moreover, such a pen may be provided in a specialized surgical procedure kit generally comprising the pen, at least one surgical drape, and a measuring device such as a scale or caliper. The kit may also comprise a volume of intravenous ICG along with any other accessories as desired. The kit may comprise an infrared fluoroscope.

DETAILED DESCRIPTION OF THE INVENTION

One example of a surgical pen is comprised of a surgical marking pen having a specific ink or fluid which is compatible with a fluorescence camera. The surgical marking pen may be used specifically to create marks on surgical sites that can be seen by both the naked eye as well as the fluorescence camera and displayed simultaneously with diagnostic information from the camera system. A kit including the pen and other supplies that are useful to the diagnostic procedure are also included.

Many fluorescing dyes have a limited fluorescing lifetime once dissolved into solution. Consequently, making a fluorescing surgical marker is not simply a case of adding a fluorescing dye to a commercially available surgical marking pen.

Figure 1:
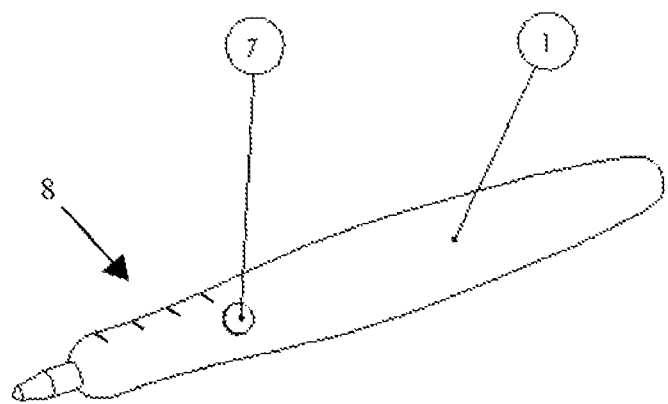
FIG. 1 shows a pen made from a flexible polymer.
Figure 2:
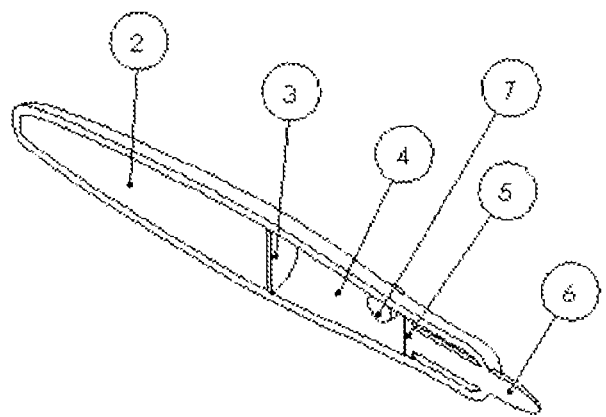
FIG. 2 shows chamber containing a solute, a separation membrane, a chamber containing visible and invisible fluorescing dye media, a filter, an injection septum, and a porous marking tip.

An example of a pen 1 is shown in one embodiment in the perspective view of FIG. 1 that may be used to keep the fluorescent dye in a shelf-life safe condition until the user activates the pen 1. The body of the pen 1 itself may have a cap where the flexible body and or cap may be optionally marked with a scale 8 or gradations if so desired, as shown. The pen 1 may be maintained sterile as well until used upon the patient. The cross section of pen 1 is shown in FIG. 2. First chamber 2 contains a measured amount of solute (e.g., 5 ml) and is separated from second chamber 4 that may contain dry dye components which are visible to the user without aid (e.g., gentian violet, bonnie's blue, brilliant green, silver nitrate, aniline dye, and combinations thereof) separated from one another by, e.g., a breakable membrane 3. If the dye is visible without aid, it may be visualized, e.g., upon the skin surface of the patient, without the use of any additional or specialized equipment but may be viewed with the user's naked eye. Alternatively, the dye component may be comprised of one or more invisible fluorescing dyes (e.g., cyanine, phthalocyanine, oxazine, rhodamine dye, and combinations thereof) where the dye may appear invisible to the user when viewed without any additional or specialized equipment but may be visualized by the user when viewed with, e.g., a fluorescence camera or imager such as the SPY® imaging system. In the event that an invisible fluorescing dye is used in the pen 1, an additional dye which is visible without aid to the user may also be incorporated such that the ink or marking may be visualized without aid when marked upon the skin surface or tissue surface.

In other embodiments, either the mixed dye component or the solute may incorporate fluorescing material. For example, stabilized fluorescing dyes may be pre-mixed with the visible dyes for a limited shelf life. In some examples, the dye formulation can include, e.g., 0.5% visible dye, 0.5% fluorescing dye, 47.0% alcohol, and water (a.q.) by volume.

Squeezing, striking, or bending the pen 1 ruptures the membrane 3 putting first and second chambers 2 and 4 in fluid communication. The user can shake the pen 1 to mix the solution. Once mixed, the ink solution can self wick or be forced through filter 5 where the mixed ink solution is homogenized and large, undissolved particles are captured before wicking into the porous marking tip 6. The filter 5 may have a plurality of pores each having a size of between, e.g., 5 and 100 microns.

The mixed dye component and/or solute, when marked on a patient's skin, may be visible to the user with the naked eye and without the use of any specialized equipment. In this manner, the user may mark the skin surface or tissue for any number of surgical procedures. In addition to the visibility of the mixed ink with the naked eye, the dye and/or solute may also fluoresce unlike conventional surgical markers when visualized under a fluorescence camera such as the SPY® imager.

In another embodiment, the solute in first chamber 2 is contained in a breakable capsule that when broken, the solute is released into the second chamber 4 containing the dry dyes forming the ink solution.

In yet another embodiment, the dry dyes are contained in a capsule contained within the solute. When broken, the solute comes in contact with the dyes to form the ink solution.

In yet another embodiment, the solute may contain the visible dye, separate from the dry fluorescing dye while in other embodiments, the fluorescing dye may be injected through a septum 7 into the pen prior to use.

The user can mark tissues immediately after preparation using the same techniques as with a typical surgical pen. Since the dyes remain undissolved until just before use, the fluorescent properties remain active over the course of the procedure.

Providing the pen within a kit of other procedure accessories, such as volume of intravenous ICG and solution and draping simplifies the treatment planning and ensures its availability for use during the procedure. Such kits may also include, e.g., a measuring device such as a scale or caliper.

What is claimed is:

1. A surgical marking pen, comprising:
   a pen body;
   a first chamber within the pen body containing at least one powdered dye;
   a second chamber within the pen body and separated from the first chamber, the second container containing a solvent, the first chamber and the second chamber being selectively placeable into fluid communication with one another; and
   a tip in fluid communication with the first chamber or the second chamber,
   wherein the at least one powdered dye and the solvent, when mixed, form a dye solution which is disposable upon a skin or tissue surface and is able to be visualized simultaneously by a user in ambient light and with a fluorescence imager.

2. The pen of claim 1, further comprising a filter between the tip and the first chamber or the second chamber, the filter being configured to homogenize the dye solution and to filter any particulates before the dye solution enters the tip.

3. The pen of claim 2, wherein the filter comprises a plurality of pores having a size between 5 and 100 microns.

4. The pen of claim 1, wherein the at least one powdered dye contains one or more dyes visible upon the skin or tissue surface in ambient light.

5. The pen of claim 4, wherein the at least one powdered dye is selected from the group consisting of gentian violet, bonnie's blue, brilliant green, silver nitrate, aniline dye, and combinations thereof.

6. The pen of claim 1, wherein the at least one powdered dye comprises one or more invisible fluorescing dyes.

7. The pen of claim 6, wherein the one or more invisible fluorescing dyes is selected from the group consisting of cyanine, phthalocyanine, oxazine, rhodamine dye, and combinations thereof.

8. The pen of claim 1, wherein the pen is sterile.

9. The pen of claim 1, wherein the pen body and/or a cap for receiving the pen body is marked with a scale.

10. A surgical procedure kit, comprising:
    the pen as in claim 1; and
    a volume of intravenous ICG.

11. The kit of claim 10, further comprising at least one surgical drape.

12. The kit of claim 10, further comprising a measuring device comprising a scale or a caliper.

13. The kit of claim 10, further comprising an infrared fluoroscope.

14. The pen of claim 1, wherein the first chamber is configured to maintain the at least one powdered dye in a shelf-life safe condition until the at least one powdered dye is mixed with the solvent.

15. A surgical marking pen, comprising:
    a pen body;
    a first chamber within the pen body containing at least one fluorescing dye;
    a second chamber within the pen body and separated from the first chamber, the second container containing a solvent, the first chamber and the second chamber being selectively placeable into fluid communication with one another; and
    a tip in fluid communication with the first chamber or the second chamber, wherein
    the first chamber is configured to maintain the at least one fluorescing dye in a shelf-life safe condition until the at least one fluorescing dye is mixed with the solvent, and
    the at least one fluorescing dye and the solvent, when mixed, form a dye solution which is disposable upon a skin or tissue surface and is able to be visualized simultaneously by a user in ambient light and with a fluorescence imager.

16. The pen of claim 15, further comprising a filter between the tip and the first chamber or the second chamber, the filter being configured to homogenize the dye solution and to filter any particulates before the dye solution enters the tip.

17. The pen of claim 16, wherein the filter comprises a plurality of pores having a size between 5 and 100 microns.

18. The pen of claim 15, wherein the at least one fluorescing dye contains one or more dyes visible upon the skin or tissue surface in ambient light.

19. The pen of claim 18, wherein the one or more dyes visible upon the skin or tissue surface is selected from the group consisting of gentian violet, bonnie's blue, brilliant green, silver nitrate, aniline dye, and combinations thereof.

20. The pen of claim 15, wherein the at least one fluorescing dye comprises one or more invisible fluorescing dyes.

21. The pen of claim 20, wherein the one or more invisible fluorescing dyes is selected from the group consisting of cyanine, phthalocyanine, oxazine, rhodamine dye, and combinations thereof.

22. The pen of claim 15, wherein the pen is sterile.

23. The pen of claim 15, wherein the pen body and/or a cap for receiving the pen body is marked with a scale.

24. A surgical procedure kit, comprising:
   the pen as in claim 15; and
   a volume of intravenous ICG.

25. The pen of claim 15, wherein the at least one fluorescing dye is a powdered dye.

26. The pen of claim 15, wherein the solvent comprises at least one dye visible in ambient light.

27. The pen of claim 1, wherein the solvent comprises at least one dye visible in ambient light.

* * * * *